United States Patent [19]

Weiss

[11] Patent Number: 5,208,244

[45] Date of Patent: May 4, 1993

[54] METHOD OF SELECTIVELY INHIBITING CALCIUM-INDEPENDENT MYOCARDIAL PHOSPHOLIPASE A2

[75] Inventor: Randy H. Weiss, St. Louis, Mo.

[73] Assignee: Washington University, St. Louis, Mo.

[21] Appl. No.: 591,583

[22] Filed: Oct. 2, 1990

[51] Int. Cl.[5] .................... A61K 31/44; A61K 31/35; A61K 31/34
[52] U.S. Cl. .................... 514/336; 514/460; 514/473
[58] Field of Search .................... 514/460, 473, 336

[56] References Cited

U.S. PATENT DOCUMENTS 4,602,006 7/1986 Krantz et al. .................... 514/63

OTHER PUBLICATIONS

Krafft, G. A. J. Am. Chem. Soc. 103(18):5459–5466 (1981) [CA 95(15) 132580].

Primary Examiner—Frederick E. Waddell
Assistant Examiner—Diane Gardner

[57] ABSTRACT

Inhibition of calcium-independent myocardial phospholipase $A_2$ is shown for compounds of the formula:

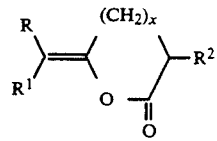

wherein R and $R^1$ independently represent hydrogen and halogen, alkyl, alkenyl and alkynyl radicals; $R^2$ represents aryl, aryloxy, and heteroaryl radicals; and X is 1 or 2.

15 Claims, No Drawings

METHOD OF SELECTIVELY INHIBITING CALCIUM-INDEPENDENT MYOCARDIAL PHOSPHOLIPASE A2

BACKGROUND OF THE INVENTION

1. Field of the Invention

The present invention relates to selective inhibition of calcium-independent myocardial phospholipase $A_2$ ($PLA_2$). More particularly, the present invention relates to a method of inhibiting calcium-independent myocardial $PLA_2$, without inhibiting other calcium-dependent mammalian $PLA_2$ enzymes, utilizing certain substituted enol lactones as selective inhibitors.

2. Background Related Art $PLA_2$ catalyzes the hydrolysis of the sn-2 ester group of membrane phospholipids to give a lysophospholipid and a free fatty acid, as illustrated in equation (1) for the hydrolysis of a diacylphosphatidylcholine. Evidence has accumulated for a potential role of $PLA_2$ in myocardial injury to the ischemic heart.

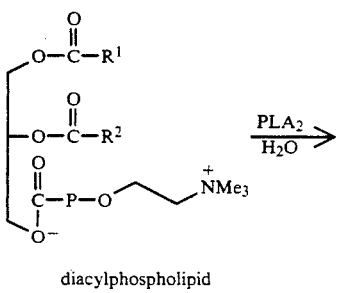

diacylphospholipid

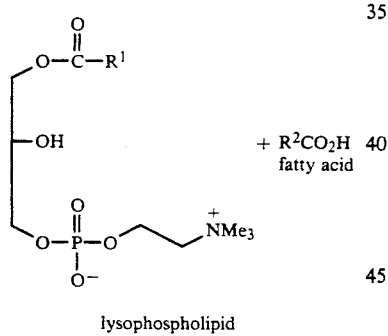

lysophospholipid

For example, it has been shown that endogenous fatty acids increase several fold in an ischemic dog heart in vivo and in isolated perfused ischemic rat and dog hearts. See, for example, van der Vusse et al, Circ. Res. 50, 538-46 (1982); Chien et al, Circ. Res., 54, 313-22 (1984); Burton et al, Am. J. Pathol., 124, 238-45 (1985). It has also been shown that lysophospholipids accumulate 2 to 3 fold in the ischemic cat heart in vivo, Corr. et al, J. Clin. Invest., 83, 927-36 (1989). The accumulation of the products of phospholipid hydrolysis implies that a $PLA_2$ may become activated in the ischemic heart.

Lysophospholipids have also been implicated as potential mediators of sudden cardiac death, Corr et al, "Lethal Arrhythmias Resulting from Myocardial Ischemia and Infarction", Rosen & Patti, eds., Kluwer Academic Publishers, Boston, 91-014 (1989). The addition of lysophospholipids to normoxic myocardial tissue in vitro induces electrophysiological alterations that are similar to those observed in the ischemic heart in vivo Corr et al, Circ. Res, 55, 135-54 (1984).

Most importantly, lysophospholipid accumulation in the ischemic dog heart in vivo has been correlated with the frequency of cardiac arrhythmias, Kinnaird et al, Lipids, 23, 32-35 (1988). Furthermore, it is known that the carnitine acyltransferase 1 inhibitor, 2-[5-(4-chlorophenyl)-pentyl]-oxirane-2-carboxylate (POCA), prevents the onset of ventricular fibrillation and ventricular tachycardia and inhibits the accumulation of lysophospholipids (and long-chain aoyloarnitines) in the ischemic cat heart in vivo, Corr et al, J. Clin. Invest., 83, 927-36 (1989).

Accelerated phospholipid catabolism by $PLA_2$ has also been implicated as a cause of infarct damage in the ischemic heart. In the ischemic heart, ATP levels decrease. Treatment of rat neonatal myocytes with the glycolytic inhibitor iodoacetate lowers the levels of ATP which results in the release of arachidonic acid and morphological alterations of the myocytes, Chien et al, J. Clin. Invest., 75, 1770-80 (1985). One $PLA_2$ inhibitor (U26,384) prevented the release of arachidonic acid, phospholipid degradation, sarcolemmal membrane defects and the release of creatine kinase that was induced by the treatment of rat neonatal myocytes with iodoacetate, Sen et al, J. Clin. Invest., 82, 1333-38 (1988).

Therefore, inhibition of myocardial $PLA_2$ activity, without inhibiting other mammalian $PLA_2$ enzymes, to prevent the accumulation of arrhythmogenic lysophospholipids in an ischemic heart is a potential therapeutic approach for the prevention of arrhythmias, infarct damage and sudden death.

SUMMARY OF THE INVENTION

The present invention is directed to a method of selectively inhibiting calcium-independent myocardial $PLA_2$ utilizing an enol lactone inhibitor compound having the formula:

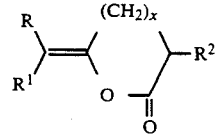

wherein R and $R^1$ independently represent hydrogen and radicals selected from the group consisting of halogen, and alkyl, alkenyl and alkynyl radicals. $R^2$ represents hydrogen and radicals selected from the group consisting of aryl, aryloxy, and heteroaryl radicals; and x represents 1 or 2.

DETAILED DESCRIPTION OF THE INVENTION

The $PLA_2$ inhibitors suitable for use in the present invention include those represented by the formula:

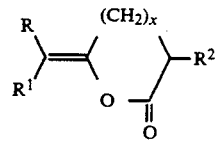

wherein R, $R^1$, $R^2$ and x are as defined above.

As utilized herein, the term "alkyl" means a straight-chain or branched chain alkyl radical having from about 2 to about 8 carbon atoms, preferably from about 2 to about 4 carbon atoms, which radical may be cyclic. The term "alkenyl" means a straight-chain or branched-chain alkyl radical of 2 to about 8 carbon atoms having ethylenic unsaturation, which radical may be cyclic. The term "alkynyl" means a straight-chain or branched-chain alkyl radical of 2 to about 8 carbon atoms having ethynyl unsaturation, which radical may be cyclic. Examples of such alkyl, alkenyl and alkynyl radicals include ethyl, n-propyl, isobutyl, t-butyl, sec-butyl, n-butyl, pentyl, iso-amyl, hexyl, octyl, 1-propenyl, 2-propenyl, 2-isobutenyl, 1-pentenyl, ethynyl, butynyl, cyclopentyl, cyclohexyl, cyclohexenyl, cyclooctynyl and the like. The term "aryl", alone or in combination, means a phenyl or naphthyl radical The term "aryloxy" means an aryl ether radical wherein the term aryl has the meaning given above. Examples of aryloxy radicals include phenoxy and 2-naphthyloxy. The term heteroaryl is an aromatic monocyclic, bicyclic or tricyclic heterocycle which contains one or more heteroatoms. Examples of such heteroaryl radicals include pyridyl, quinolyl, furyl, thienyl, oxazolyl. The term halogen means chlorine, bromine and iodine.

A preferred class of compounds for use in the present invention is one wherein R and $R^1$ independently represent hydrogen and radicals selected from the group consisting of halogen and alkynyl radicals; $R^2$ represents hydrogen and phenyl, phenoxy, pyridyl and naphthyl radicals; and x is 2.

A most preferred class of compounds for use in the method of the present invention is the class wherein R represents bromo and iodo radicals and an ethynyl radical; $R^1$ represents hydrogen; $R^2$ represents naphthyl; and x is 2.

The subject inhibitors can be prepared utilizing the methods described by Daniels et al, J. Biol. chem., 258, 15046-53 (1983), Hummel et al, Liebigs Ann. Chem., 746, 211-13 (1971); Daniels et al, Biochemistry, 25 1436-44 (1986); Holland et al, Synth. Commun., 4, 203 (1974); Kraft et al, J. Am. Chem. Soc., 103 5459-66 (1981); and those set forth below in Examples 1-10. These references are incorporated herein by reference.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

All reagents were used as received without purification. All proton and carbon NMR spectra were obtained on either a Varian VXR-300 or VXR-400 nuclear magnetic resonance spectrometer.

EXAMPLE 1

A. Synthesis of 1-Bromo-3-butyne

This compound was prepared following the procedure of Daniels et al, J. Biol. Chem. 258, 15046-15053 (1983). Over a dry argon atmosphere in an oven-dried apparatus, a solution of phosphorus tribromide (48 mL, 0.51 mol) in anhydrous ether (130 mL) was added over a period of 3 h to a stirred solution of 3-butyn-1-ol (99.5 g, 1.24 mol) in ether (750 mL) at 0° C. After addition was complete, the reaction mixture was poured carefully onto ice (1000 g). The ether layer was collected and the aqueous layer was extracted with ether. The ether layers were combined and washed with saturated $NaHCO_3$, $H_2O$, saturated NaCl, and $H_2O$. The ether layer was dried ($MgSO_4$). The ether was distilled off at atmospheric pressure. 1-Bromo-3-butyne was distilled off at atmospheric pressure as a colorless liquid (45 g, 27% yield). The $^1H$ NMR was consistent with the literature spectrum:

bp 109°-112° C., lit bp 110°-112° C.; 300 mHZ $^1H$ NMR ($CDCl_3$) δ2.12 (t, J=3.0 Hz, 1H), 2.76 (dt, J=7.5, 3.0 Hz, 2H), 3.45 (t, J=7.5 Hz, 2H).

B. Synthesis of α-(3-Butynyl)-1-naphthaleneacetic Acid

This compound was prepared following the procedure of Daniels et al J. Biol. Chem. 258, 15046-15053 (1983). Diisopropylamine (102 mL, 73.6 g, 0.727 mol) was added to a stirred solution of 1.6M n-butyllithium in hexanes (488 mL, 0.761 mol) at 0° C. under argon in a flame-dried apparatus. The light yellowish-brown solution was stirred for 2 h at 0° C. A solution of 1-naphthaleneacetic acid (65.9 g, 0.354 mol) in anhydrous THF (355 mL) was added to the stirred lithium diisopropylamide solution at −78° C. and was then stirred 3.5 h at 0° C. A red precipitate formed. Hexamethylphosphoramide (71 mL) was added to the mixture at 0° C. to dissolve the precipitate. The mixture became deep red.

A solution of the 1-bromo-3-butyne of Part A (49.5 g, 0.372 mol) in THF (355 mL) was added to the stirred mixture at −78° C. The mixture was stirred for 1 h at −78° C. and then allowed to warm to room temperature. The mixture was stirred for 24 h at room temperature. The reaction was quenched with 3N HCl to pH 2 at 0° C. The organic phase was collected and the aqueous phase was extracted with ether (2×equal volumes). The combined organic layers were washed with $H_2O$ to remove hexamethylphosphoramide. The organic phase was dried ($MgSO_4$) and the solvent was removed in vacuo to give a yellowish oil weighing 87.7 g.

The crude oil was purified by flash chromatography in portions (24 g). The residue was dissolved in $CHCl_3$ and applied to a 7.5×40 cm silica gel (Aldrich catalog #22,719-6, 230-400 mesh) column that was pre-equilibrated with $CHCl_3$. The column was eluted with 5 L of $CHCl_3$, followed by 1 L of ethyl acetate/$CHCl_3$ (2:98, v/v), and finally 4 L of ethyl acetate/acetic acid/$CHCl_3$ (5:1:94, v/v/v). Fractions which eluted with ethyl acetate/acetic acid/$CHCl_3$ and having a single spot with $R_f=0.75$ on Bakerflex silica gel IBF-2 TLC plates (developed in ethyl acetate/acetic acid/$CHCl_3$, 5:1:94, v/v/v) were combined. The solvent was removed in vacuo to give 12.6 g (55% yield) of the product as a white solid. The $^1H$ NMR was consistent with the literature spectrum:

300 mHz $^1H$ NMR ($CDCl_3$) δ2.04 (t, J=3.0 Hz, 1H), 2.29 (m, 4H), 4.67 (t, J=6.0 Hz, 1H), 7.50 (m, 4H), 7.84 (m, 2H), 8.17 (m, 1H).

C. Synthesis of Tetrahydro-(E)-6-(iodomethylene)-3-(1-naphthalenyl)-2H-pyran-2-one This compound was prepared following the procedure of Daniels et al. J. Biol. Chem. 258, 15046-15053 (1983). A solution of the α-(3-butynyl)-1-naphthaleneacetic acid of Part B (0.98 g, 4.1 mmol), potassium bicarbonate (0.42 g, 4.2 mmol) and iodine (1.06 g, 4.19 mmol) in $CH_3CN$ (120 mL) was stirred at room temperature for 21 h in the dark. The purple solution was treated with 5% $Na_2S_2O_3$ to remove residual iodine The mixture was extracted with $CH_2Cl_2$ (4×100 mL). The combined extracts were dried ($MgSO_4$) and the solvent was removed in vacuo to give a residue weighing 0.8 g.

The residue was dissolved in $CH_2Cl_2$ and applied to a 4×10 cm silica gel (Aldrich catalog #22,719-6, 230–400 mesh) column pre-equilibrated with $CH_2Cl_2$/hexane (60:40, v/v). The column was eluted under pressure (flash chromatography) with $CH_2Cl_2$/hexane (60:40, v/v). Fractions which gave a single UV spot with $R_f=0.35$ on Bakerflex IB2-F silica TLC plates (developed in $CH_2Cl_2$/hexane. 60:40. v/v) were combined. The solvent was removed in vacuo to give 0.41 g (27% yield) of the iodoenol lactone as a light yellow wax. The $^1H$ NMR and mass spectra were consistent with the literature spectra. Proton NOE (nuclear Overhauser effect) studies confirmed the trans configuration of the iodide relative to the lactone oxygen:

300 mHz $^1H$ NMR ($CDCl_3$) δ2.35 (m, 2H), 2.82 (m, 2H), 4.54 (dd, J=8.1, 6.6 Hz, 1H), 6.09 (t, J=1.5 Hz, 1H), 7.30 (d, J=7.2 Hz, 1H), 7.50 (m, 3H), 7.86 (m, 3H); 75 mHz $^{13}C$ NMR ($CDCl_3$) δ168.27, 153.36, 134.15, 133.34, 130.78, 129.33, 128.72, 126.67, 125.93, 125.78, 125.31, 122.71, 60.47, 43.97, 26.42, 25.63; electron impact mass spectrum (70 eV) m/z (relative intensity) 364 (20, M+), 209 (40), 181 (15), 167 (100), 152 (50); chemical ionization mass spectrum ($CH_4$) m/z 365 $(M+H)^+$.

EXAMPLE 2

A. Synthesis of Tetrahydro-3-(1-Naphthalenyl)-(E)-6-[3-(trimethylsilyl)prop-2-ynylidene]-2H-pyran-2-one To a stirred mixture of iodoenol lactone prepared as in Example 1C (330 mg, 0.906 mmol) in anhydrous triethylamine (10 mL) was added bis(triphenylphosphine)-palladium(II) chloride (12.7 mg, 0.016 mmol) and cuprous chloride (7.1 mg, 0.071 mmol) at room temperature in a flame-dried apparatus over a dry argon atmosphere. To the cloudy mixture was added trimethylsilylacetylene (0.132 mL, 0.937 mmol) at room temperature. The mixture was stirred vigorously for 4 h. The solvent and volatile materials were removed in vacuo. The residue was triturated with toluene. The triturate was filtered through glass wool and the solvent was removed in vacuo to give 0.5 g of an orange oil.

The oil was purified by flash chromatography with a 2×25 cm silica gel (Aldrich catalog #28,863-2, 70–230 mesh) column using $CH_2Cl_2$/hexane (50:50, v/v) as eluant. Fractions containing one UV active spot with $R_f=0.15$ on Bakerflex IBF-2 silica TLC plates (developed with $CH_2Cl_2$/hexane, 50:50, v/v) were combined and the solvent was removed in vacuo to give 182 mg (67% yield) of product as an orange oil:

300 mHz $^1H$ NMR ($CDCl_3$) δ0.20 (s, 9H), 2.34 (m, 2H), 2.83 (m, 1H), 3.00 (m, 1H), 4.58 (t, J=7.2 Hz, 1H), 5.46 (s, 1H), 7.31 (d, J=6.6 Hz, 1H), 7.50 (m, 3H), 7.85 (m, 3H); 75 mHz $^{13}C$ NMR ($CDCl_3$) δ168.31, 161.48, 134.28, 133.82, 130.76, 129.42, 128.79, 126.77, 126.07, 126.01, 125.41, 122.84, 100.61, 99.43, 92.12, 44.86, 25.55, 23.80, 0.06; electron impact mass spectrum (70 eV) m/z (relative intensity) 334 (20, M+), 319 , (7), 306 (25), 153 (100); chemical ionization mass spectrum (CH<) m/z 335 $(M+H)^+$.

B. Synthesis of Tetrahydro-3-(1-Naphthalenyl)-(E)-6-(prop-2-ynylidene)-2H-pyran-2-one To a stirred solution of the product of Part A (1.29 g, 3.86 mmol) in ethyl alcohol (20 mL) was added quickly a solution of silver nitrate (2.63 g, 15.5 mmol) in $H_2O$ (21 mL) at room temperature over argon. The mixture was stirred for 1 h at room temperature. $CH_2Cl_2$ (20 mL) was added and an orange precipitate formed. The entire mixture was poured into a stirred solution of potassium cyanide (6.0 g, 92 mmol) in $H_2O$ (60 mL). The mixture was stirred for 1 h at room temperature. The mixture was extracted with $CH_2Cl_2$(3×120 mL). The combined extracts were dried ($MgSO_4$) and the solvent was removed in vacuo to give 760 mg of a viscous orange oil.

The oil was purified by preparative reverse-phase HPLC using a custom-packed (Waters) 57 mm×30 cm PrepPAK Vydac $C_{18}$ (15–20 micron) column. The column was eluted with $CH_3CN/H_2O$ (57:43, v/v) at a flow rate of 50 mL/min and a detector setting of 280 nm. The fraction corresponding to the peak eluting with a retention time of 27 min was collected and extracted with $CH_2Cl_2$. The extract was dried (MgSO<) and the solvent was removed in vacuo to give 464 mg (51% yield) of ynenol lactone as a waxy orange solid. NOE studies confirmed the trans configuration of the ethynyl group relative to the lactone oxygen:

300 mHz $^1H$ NMR ($CDCl_3$) δ2.34 (dd, J=13.5, 7.5 HZ, 2H), 2.84 (m, 1H), 3.03 (m, 1H), 3.13 (d, J=2.1 HZ, 1H), 4.59 (t, J=7.5 Hz, 1H), 5.42 (s, 1H), 7.32 (d, J=6.6 Hz, 1H), 7.50 (m, 3H), 7.86 (m, 3H); 75 mHz $^{13}C$ NMR ($CDCl_3$) δ168.09, 161.95, 134.19, 133.70, 130.69, 129.34, 128.72, 126.70, 125.97, 125.93, 125.32, 122.72, 90.82, 82.81, 78.13, 44.73, 25.46, 23.72; electron impact mass spectrum (70 eV) m/z (relative intensity) 262 (55, M+), 233 (40), 165 (60), 152 (100); exact mass (M+): calcd, 262.0993; found, 262.0987 ($C_{18}H_{14}O_2$).

EXAMPLE 3

Synthesis of (E)-6-(bromomethylene)tetrahydro-3-(1-naphthalenyl)-2H-pyran-2-one (1)

This compound was synthesized following the procedure of Daniels et al. J. Biol. Chem. 258, 15046–15053 (1983). To a stirred solution of the α-(3-butynyl)-1-naphthaleneacetic acid prepared as in Example 1B (0.57 g, 2.4 mmol) in $CH_2Cl_2$ (50 mL) was added N-bromosuccinimide (0.84 g, 4.7 mmol), potassium bicarbonate (0.54 g, 5.4 mmol) and 0.4M aqueous tetrabutylammonium hydroxide (0.74 mL, 0.30 mmol) at room temperature. The colorless mixture was stirred for 3 h at room temperature. The mixture was transferred to a separatory funnel and washed with 5% $Na_2S_2O_3$, $H_2O$, saturated aqueous NaCl, and $H_2O$. The solution was dried ($MgSO_4$) and the solvent was removed in vacuo to give a colorless oil weighing 0.84 g. $^1H$ NMR of the oil indicated that 60% of the residue was the desired bromoenol lactone.

The oil was dissolved in $CH_2Cl_2$ and applied to a pre-equilibrated 2×40 cm column packed with silica gel (Aldrich catalog #22,719-6, 230–400 mesh) in $CH_2Cl_2$/hexane (65:35, v/v). The column was eluted under pressure at a rate of 10 mL/min and 10 mL fractions were collected. Fractions 16–26 showed an UV active spot at $R_f=0.33$ on Bakerflex IBF-2 silica gel plates that were developed in $CH_2Cl_2$/hexane (65:35, v/v). The fractions were combined to give 0.41 g of a colorless oil that was about 90% lactone and 10% of two other constituents as shown by $^1H$ NMR.

The oil was purified by preparative reverse-phase HPLC using a custom-packed (Waters) 57 mm×30 cm Vydac Preppak $C_{18}$ (15–20 micron) preparative column and eluted with $CH_3CN/H_2O$ (55:45, v/v) at a flow rate of 50 mL/min. The detector was set at 280 nm. The eluant for the peak with a retention time of 40 min was collected and extracted with CH₂Cl₂. The extract was dried (MgSO₄) and the solvent was removed in vacuo to give product as a colorless oil in 43% yield. The $^1$H NMR and mass spectra were consistent with the literature spectra NOE studies confirmed the trans geometry of the bromide relative to the lactone oxygen:

300 mHz $^1$H NMR (CDCl₃) δ2.35 (m, 2H), 2.82 (m, 2H), 4.55 (dd, J=8.4, 6.6 Hz, 1H), 6.09 (t, J=1.5 Hz, 1H), 7.30 (m, 1H), 7.50 (m, 3H), 7.86 (m, 3H); electron impact mass spectrum (70 eV) m/z (relative intensity) 318/316 (M+), 290/288 (10, M+- CO), 237 (65), 209 (90).

EXAMPLE 4

Synthesis of Tetrahydro-(Z)-6-(iodomethylene)-3-(1-naphthalenyl)-2H-pyran-2-one To a stirred solution of α-(3-butynyl)-1-naphthaleneacetic acid prepared as in Example 1B (9.4 g, 39 mmol) in CH₃CN (100 mL) was added iodine (10.2 g, 40.0 mmol) and potassium bicarbonate (40 g, 40 mmol). The mixture was stirred for 50 h at room temperature. A solution of 5% Na₂S₂O₂ (300 mL) was added to remove excess iodine. The mixture was extracted with CH₂Cl₂(4×100 mL). The combined extracts were dried (MgSO₄) and the solvent was removed in vacuo.

The residue was applied to a 7.5×36 cm silica gel (Aldrich catalog #22,719-6, 230-400 mesh) column pre-equilibrated with CH₂Cl₂/hexane (50:50, v/v). The column was eluted with CH₂Cl₂/hexane (50:50, v/v) to remove most of the (E)-iodoenol lactone. Elution of the column with CH₂Cl₂/hexane (60:40, v/v) provided 0.65 g of the (Z)-iodoenol lactone as a colorless oil (5% yield). An analytical sample of the compound was obtained by semi-preparative reverse-phase HPLC using an Alltech 10×250 mm Econosil Ca (10 micron) Prep column. The column was eluted using CH₃CN/H₂O (54:46, v/v) at a flow rate of 6.0 mL/min and a detector setting of 280 nm. The fraction corresponding to the peak with a retention time of 21.3 min was collected and extracted with CH₂Cl₂. The extract was dried (MgSO₄) and the solvent was removed in vacuo. NOE studies confirmed the cis configuration of the iodide relative to the lactone oxygen.

300 mHz $^1$H NMR (CDCl₃) δ2.32 (m, 2H), 2.95 (m, 2H), 4.86 (dd, J=9.9, 6.3 Hz, 1H), 5.60 (t, J=0.9 Hz, 1H), 7.52 (m, 4H), 7.88 (d, J=7.7 Hz, 1H), 7.98 (m, 2H); electron impact mass spectrum (70 eV) m/z (relative intensity) 364 (35, M ), 237 (62), 209 (47), 181 (26), 167 (100), 152 (97); exact mass (M+): calcd, 363.9960; found, 363.9975 (C₁₆H₁₃O₂I).

EXAMPLE 5

A. Synthesis of δ-(3-Butynyl)phenylacetic Acid

This compound was prepared following a procedure by Daniels et al. J. Biol. Chem. 258, 15046-15053 (1983). A solution of phenylacetic acid (1.00 g, 7.37 mmol) in anhydrous THF (5 mL) was added dropwise to a stirred solution of lithium diisopropylamide in THF (generated from diisopropylamine (2.1 mL, 1.5 g, 15 mmol) in THF (5 mL) and 1.6 M n-butyllithium in hexanes (9.2 mL, 15 mmol) at 0° C. over argon in a flame-dried apparatus. After addition was complete, the yellow mixture was allowed to warm to room temperature and was stirred for 2 h. Hexamethylphosphoramide (2 mL) was added to dissolve the precipitate. A solution of 1-bromo-3-butyne prepared as in Example 1A (1.0 g, 0.70 mL, 7.5 mmol) in THF (5 mL) was added to the stirred solution at room temperature. The mixture was stirred for 16 h at room temperature. The reaction was quenched with 3N HCl to pH 1 and extracted with ether (3×equal volumes). The combined ether extracts were washed with H₂O (10×equal volumes). The ether layer was dried (MgSO₄) and the solvent was removed in vacuo to give 1.34 g of a white solid.

The solid was taken up in CHCl₃ and applied to a 4×15 cm silica gel (Aldrich catalog #22,719-6, 230-400 mesh) column pre-equilibrated with ethyl acetate/CHCl₃ (1:99 v/v). The column was eluted with ethyl acetate/CHCl₃ (1:99 v/v) to give 532 mg (39% yield) of product (R$_f$=0.20, Bakerflex silica IBF-2 TLC plates) as a white solid. The $^1$H NMR was consistent with the literature spectrum:

300 MHz $^1$H NMR (CDCl₃) δ1.99 (t, J=2.5 Hz, 1H), 2.16 (m, 4H), 3.80 (t, J=7.5 Hz, 1H), 7.32 (m, 5H).

B. Synthesis of (E)-6-(Bromomethylene)tetrahydro-3-phenyl-2H-pyran-2-one

This compound was prepared following a procedure by Daniels et al. (1983) J. Biol. Chem. 258, 15046-15053. A mixture of the α-(3-butynyl)phenylacetic acid of Part A (0.36 g, 1.3 mmol), KHCO₃ (0.21 g, 2.1 mmol), N-bromosuccinimide (0.38 g, 2.1 mmol) and 0.4M aqueous tetrabutylammonium hydroxide (0.61 mL, 0.24 mmol) in CH₂Cl₂(30 mL) was stirred at room temperature for 5 h. The mixture was washed with 5% Na₂SO₃, saturated NaCl, and H₂O. The CH₂Cl₂ layer was dried (MgSO₄) and the solvent was removed in vacuo to give a residue weighing 200 mg. The residue was purified by preparative reverse-phase HPLC using a custom-packed (Waters) 57 mm×30 cm PrepPAK Vydac C₁₈ a column (15-20 micron). The eluting solvent was CH₃CN/H₂O (55:45, v/v) at a flow rate of 50 mL/min. The eluant was monitored at 255 nm. The fraction corresponding to the peak with a retention time of 27 min was collected and extracted with CH₂Cl₂. The extract was dried (MgSO₄) and the solvent was removed in vacuo to give 94 mg (26% yield) of lactone product as a colorless oil. The $^1$H NMR and mass spectra were consistent with the literature spectra:

300 mHz $^1$H NMR (CDCl₃) δ2.27 (m, 2H), 2.85 (m, 2H), 4.02 (dd, J=9.5, 7.1 Hz, 1H), 6.17 (t, J=1.7 HZ, 1H), 7.33 (m, 5H); chemical ionization mass spectrum (CH₄) m/z (relative intensity) 267 (M+H)+,187 (MH-Br)+.

EXAMPLE 6

A. Synthesis of α-(2-Propynyl)-1-naphthaleneacetic Acid

This compound was prepared following a procedure of Daniels et al. Biochemistry 25, 1436-1444 (1986). To a solution of diisopropylamine (16.5 mL, 0.118 mol) in anhydrous THF (140 mL) was added 2.5M n-butyllithium in hexanes (43 mL, 0.11 mol) at 0° C. over argon. The solution was stirred for 1 h at 0° C. and then cooled to −78° C. To the stirred solution was added over a period of 1 h a solution of 1-naphthaleneacetic acid (10.0 g, 0.0537 mol) in THF (100 mL) at −78° C. The orange mixture was stirred for 1.5 h at −78° C. 1,3-Dimethyl-3,4,5,6-tetrahydro-2(1H)-pyrimidinone (10 mL) was added to dissolve the precipitate. A solution of propargyl chloride (4.1 mL, 0.056 mol) in THF (55 mL)

was added dropwise over a period of 20 min at −78° C. The orange mixture was stirred for an additional 30 min at −78° C. and then allowed to come to room temperature. The greenish brown solution was stirred for 20 h at room temperature. The reaction mixture was quenched with 1N HCl (100 mL). The layers were separated and the organic layer was washed with 1N HCl (100 mL). The aqueous layers were combined and extracted with ethyl ether (2×50 mL). The organic layers were combined and washed with saturated NaCl and saturated NaHCO$_3$. The organic layer was dried (MgSO$_4$) and the solvent was removed in vacuo to give 11.7 g of a dark brown liquid.

The liquid was applied to a 7.5×22 cm column packed with silica gel (Aldrich catalog #22,719-6, 230–400 mesh) pre-equilibrated with ether/hexane (30:70, v/v). The column was eluted under pressure with ether/hexane (30:70, v/v). Fractions which gave a UV active spot with R$_f$=0.35 (30:70 ether/hexane (v/v), Bakerflex IBF-2 TLC plates) were combined and the solvent was removed in vacuo to give 10.5 g (67% yield) of product as a white solid.

A portion of the compound was recrystallized from ethyl acetate/hexane to give white needles. The $^1$H NMR spectrum was consistent with the literature 300 mHz $^1$H NMR (CDCl$_3$) δ1.97 (t, J=2.6 Hz, 1H), 2.78 (ddd, J=16.9, 6.3, 2.7 Hz, 1H), 3.11 (ddd, J=16.9, 8.5, 2.6 Hz, 1H), 4.69 (dd, J=8.5, 6.3 Hz, 1H), 7.50 (m, 4H), 7.83 (m, 2H), 8.12 (d, J=8.2 Hz, 1H).

B. Synthesis of (E)-5-(Bromomethylene)tetrahydro-3-(1-naphthalenyl)-2(3H)-furanone This compound was prepared following a procedure of Daniels et al. Biochemistry, 1436–1444 (1986). A mixture of α-(2-propynyl)-1-naphthaleneacetic acid of Part A (665 mg, 3.07 mmol), KHCO$_3$ (320 mg, 3.2 mmol), N-bromo-succinimide (570 mg, 3.2 mmol), and 0.56M aqueous tetrabutylammonium hydroxide (0.63 mL, 0.35 mmol) in CH$_2$Cl$_2$(30 mL) was stirred at room temperature for 1.5 h. The yellow mixture was washed with 5% Na$_2$S$_2$O$_3$, H$_2$O and saturated NaCl. The organic layer was dried (MgSO$_4$) and the solvent was removed in vacuo to give an orange oil.

The oil was purified using a Chromatotron with an Analtech 4000 μm silica gel 6F plate (catalog #02206) and an eluting solvent of ether/hexane (20:80, v/v). A yellow residue was obtained weighing 250 mg (27% yield). A portion of this residue was further purified by semi-preparative reverse-phase HPLC using an Alltech 10×250 mm Econsoil C$_{18}$ (10 micron) column and eluting isocratically with CH$_3$CN/H$_2$O (55:45, v/v) at a flow rate of 6.0 mL/min (detector at 280 nm). The fraction corresponding to a peak with a retention time of 18.7 min was collected and extracted with CH$_2$Cl$_2$. The CH$_2$Cl$_2$ extract was dried (MgSO$_4$) and the solvent was removed in vacuo to give pure product. The $^1$H NMR and mass spectra were consistent with the literature spectra:

300 mHz $^1$H NMR (CDCl$_3$) δ3.05 (ddd, J=17.7, 7.1, 2.5 Hz, 1H), 3.59 (ddd, J=17.7, 10.8, 2.2 Hz, 1H), 4.57 (dd, J=10.9, 7.1, 1H), 6.13 (t, J=2.4 Hz, 1H), 7.43 (m, 4H), 7.87 (m, 3H); electron impact mass spectrum (70 eV) m/z (relative intensity) 302/304 (M+, 11/12), 223 (8), 195 (21), 153 (100); chemical ionization mass spectrum (CH$_4$) m/z 303 (M+H)+.

EXAMPLE 7

Synthesis of Tetrahydro-6-methylene-3-(1-naphthalenyl)-2H-pyran-2-one

This compound was prepared following a procedure of Daniels et al. Biochemistry 1436–1444 (1986). To a solution of α-(3-butynyl)-1-naphthaleneacetic acid prepared as in Example 1B (305 mg, 1.28 mmol) in CH$_2$Cl$_2$(24 mL) was added mercuric trifluoroacetate (54.4 mg, 0.128 mmol). The mixture was stirred for 23 h at room temperature. The mixture was washed with H$_2$O and saturated NaCl and dried (MgSO$_4$). The solvent was removed in vacuo. The residue was purified by flash chromatography using a 2 cm diameter column and 15 g of silica gel (Aldrich catalog #22,719-6, 230–400 mesh). The column was eluted with ether/hexane (20:80, v/v). The fractions containing an UV active compound with R$_f$=0.29 (20:80 (v/v) ether/hexane, Bakerflex IBF-2 silica TLC plates) were combined. The solvent was removed in vacuo to give 167 mg (55% yield) of the lactone product as a colorless oil.

The oil could be further purified by semi-preparative reverse-phase HPLC using isocratic conditions of CH$_3$CN/H$_2$O (50:50, v/v) at a flow rate of 6.0 mL/min (detector at 280 nm). The fraction corresponding to the peak eluting at 17.6 min was collected and extracted with CH$_2$Cl$_2$. The extract was dried (MgSO$_4$) and the solvent was removed in vacuo. The $^1$H NMR and mass spectra were consistent with the literature spectra:

300 mHz $^1$H NMR (CDCl$_3$) δ2.30 (m, 2H), 2.65 (m, 2H), 4.42 (s, 1H), 4.55 (d, J=8.7, 6.6 Hz, 1H), 4.82 (s, 1H), 7.45 (m, 4H), 7.86 (m, 3H); electron impact mass spectrum (70 eV) m/z (relative intensity) 238 (M+, 100), 210 (51), 192 (10), 181 (24), 167 (65), 152 (91), 141 (21), 128 (12), 115 (13); chemical ionization mass spectrum (CH$_4$) m/z 239 (M+H)+.

EXAMPLE 8

A. Synthesis of α-(3-Butynyl)phenoxyacetic Acid

In a flame-dried apparatus, a solution of 2.5 M n-butyllithium in hexanes (23.5 mL, 58.8 mmol) was added to a stirred solution of anhydrous diisopropylamine (8.24 mL, 5.95 g, 58.8 mmol) in anhydrous THF (20 mL) at 0° C. over argon. The mixture was allowed to warm to room temperature and after 10 min was cooled to −78° C. A solution of phenoxyacetic acid (2.24 g, 14.7 mmol) in THF (8 mL) was added to the stirred mixture at −78° C. The yellow mixture was stirred for 15 min at −78° C. A solution of 1-bromo-3-butyne, prepared as in Example 1A, (2.8 mL, 4.0 g, 30 mmol) in THF (8 mL) was added to the stirred solution at −78° C. The mixture was stirred for 1 hour at −78° C. and was then poured onto ice (300 g). The pH of the mixture was adjusted to 2 with 3N HCl. The acidified mixture was extracted with ether (5×250 mL). The combined extracts were dried (MgSO$_4$) and the solvent was removed in vacuo to give a white residue.

The residue was purified by preparative reverse phase HPLC using a custom-packed (Waters) 57 mm×30 cm PrepPAK Vydac C$_{18}$ (15–20 micron) column. The column was eluted with CH$_3$CN/H$_2$O (60/40, v/v) at a flow rate of 50 mL/min and a detector setting of 270 nm. The fraction corresponding to the peak eluting with a retention time of 25 min was collected and extracted with CH$_2$Cl$_2$. The extract was dried (MgSO$_4$) and the solvent was removed in vacuo to give 129 mg (9% yield) of product as a white solid. An analytical sample was obtained by recrystallization from $CH_2Cl_2$/hexane to give white needles:

mp 92°–93° C.; 300 mHz $^1$H NMR ($CDCl_3$) δ1.99 (t, J=2.6 Hz, 1H), 2.20 (m, 2H), 2.48 (m, 2H), 4.84 (t, J=6.4 Hz, 1H), 6.92 (d, J=7.8 Hz, 2H), 7.00 (t, J=6.9 Hz, 1H), 7.28 (m, 2H); 75 mHz $^{13}$C NMR ($CDCl_3$) δ176.64, 157.49, 129.70, 122.21, 115.36, 82.28, 74.52, 69.78, 31.54, 14.64; electron impact mass spectrum (70 eV) m/z (relative intensity) 204 (100, M+), 159 (40). Anal Calcd for $C_{12}H_{11}BrO_3$, 70.60; H, 5.92. Found: C, 70.83; H, 5.77.

B. Synthesis of (E)-6-(Bromomethylene)tetrahydro-3-phenoxy-2H-pyran-2-one

A mixture of the α-(3-butynyl)phenoxyacetic acid of Part A, (74 mg, 0.36 mmol), N-bromosuccinimide (132 mg, 0.720 mmol), potassium bicarbonate (98 mg, 0.90 mmol) and 0.4M aqueous tetrabutylammonium hydroxide (0.11 mL, 0.044 mmol) in $CH_2Cl_2$(8 mL) was stirred at room temperature in the dark for 7 h. The mixture was washed with 5% $Na_2S_2O_3$ and saturated NaCl. The organic layer was dried ($MgSO_4$) and the solvent was removed in vacuo to give 42 mg of an oil.

The crude oil was purified by preparative reverse-phase HPLC using a custom-packed (Waters) 57 mm×30 cm PrepPAK Vydac $C_{a18}$ (15–20 micron) column. The column was eluted with $CH_3CN/H_2O$ (60:40, v/v) at a flow rate of 50 mL/min and a detector setting at 270 nm. The fraction corresponding to the peak eluting with a retention time of 8.4 min was collected and extracted with $CH_2Cl_2$. The extract was dried ($MgSO_4$) and the solvent was removed in vacuo to give 6 mg (6% yield) of the product as a colorless oil:

300 mHz $^1$H NMR ($CDCl_3$) δ2.23 (m, 1H), 2.48 (m, 1H), 2.98 (m, 2H), 5.41 (dd, J=10.9, 5.3 Hz, 1H), 6.21 (t, J=1.9 Hz, 1H), 7.02 (m, 3H), 7.30 (m, 2H); electron impact mass spectrum (70 eV) m/z (relative intensity) 282/284 (18/15, M+), 254/256 (42/40), 175 (4), 161/163 (65/56); exact mass (M+): calcd, 283.1287; found, 283.1299 ($C_{12}H_{11}BrO_3$).

EXAMPLE 9

A. Synthesis of 5-Hexynoic Acid

This compound was prepared following the procedure set forth in Holland et al, Synth. Commun., 4, 203 (1974). A solution of 5-hexyn-1-ol (5.00 g, 50.9 mmol) in acetone (60 mL) was added to a stirred solution of chromium trioxide (10.0 g, 102 mmol) in 5M $H_2SO_4$(125 mL) at 5°–10° C. The solution's color changed from orange to a dark blue-green. After stirring for 2.5 h at room temperature, the acetone was removed in vacuo. $H_2O$ (1000 mL) was added and the mixture was extracted with ether (6×50 mL). The combined ether extracts were washed with $H_2O$. The ether layer was extracted with 3N NaOH (2×100 mL). The basic extract was washed with ether. The basic layer was cooled to 0° C. and acidified with 3N HCl to pH 2. The acidic solution was extracted with $CH_2Cl_2$(4×75 mL). The $CH_2Cl_2$extract was dried ($Na_2SO_4$) and the solvent was removed in vacuo to give a colorless liquid.

The liquid was applied to a 5×20 cm silica gel (Aldrich catalog #22,719-6, 230–400 mesh) column pre-equilibrated with ethyl acetate/hexane (30:70, v/v). The column was eluted under pressure with ethyl acetate/hexane (30:70, v/v) to give 4.1 g (72% yield) of product as a colorless liquid:

300 mHz $^1$H NMR ($CDCl_3$) δ1.77 (m, 2H), 2.25 (dt, J=7.0, 2.7 Hz, 2H), 2.34 (t, J=2.6 Hz, 1H), 2.41 (t, J=7.3 Hz, 2H).

B. Synthesis of (E)-6-(Bromomethylene)tetrahydro-2H-pyran-2-one

This compound was prepared according to the procedure set forth in Kraft et al, J. Am. Chem. Soc., 103, 5459–5466 (1981). A mixture of the 5-hexynoic acid of Part A (1.1 g, 9.8 mmol), $KHCO_3$ (1.5 g, 15 mmol), N-bromosuccinimide (2.6 g, 15 mmol) and 0.4M aqueous tetrabutylammonium hydroxide (2 mL, 0.8 mmol) in $CH_2Cl_2$(90 mL) was stirred at room temperature for 3.5 h. The mixture was washed with 5% $Na_2S_2O_3$ and saturated NaCl. The organic phase was dried ($MgSO_4$) and the solvent was removed in vacuo to give a residue weighing 1.8 g. The residue was purified by flash chromatography (silica gel, Aldrich catalog #22,719-6, 230–400 mesh). The column was eluted with $CH_2Cl_2$and fractions having a spot with $R_f$=0.32 ($CH_2Cl_2$, Bakerflex IBF-2 silica TLC plates) were combined. The solvent was removed in vacuo to give 1.0 g (58% yield) of product as a colorless oil.

The residue was further purified by semi-preparative reverse-phase HPLC using an Analtech 10×250 mm Econosil $C_{18}$ (10 micron) column. The eluting solvent was $CH_3CN/H_2O$ (50:50, v/v) at a flow rate of 6.0 mL/min with a detector setting of 220 nm. The fraction corresponding to the peak with a retention time of 5.1 min was collected and extracted with $CH_2Cl_2$. The extract was dried ($MgSO_4$) and the solvent was removed in vacuo. Recovery off of the column was 78%. The residue was further purified by semi-preparative reverse-phase HPLC using a mobile phase of $CH_3CN/H_2O$ (30:70, v/v) at a flow rate of 6.0 mL/min. The fraction corresponding to the peak with a retention time of 19.1 min was collected and worked up as before to give pure product (69% recovery off of the column) as a colorless oil. The $^1$H NMR was consistent with the literature spectrum:

300 mHz $^1$H NMR ($CDCl_3$) δ1.95 (m, 2H), 2.65 (t, J=6.7 Hz, 2H), 2.70 (m, 2H), 6.06 (t, J=1.6 Hz, 1H).

EXAMPLE 10

A. Synthesis of 3-Butynyl Triflate

The compound was prepared following a procedure of Hummel et al. Liebigs Ann. Chem. 746, 211–213 (1971). Anhydrous pyridine (20.0 mL, 19.6 g, 0.248 mol) was added to a stirred solution of trifluoromethanesulfonic anhydride (70.0 g, 0.248 mol) in anhydrous $CH_2Cl_2$(500 mL) at 0° C. over a dry nitrogen atmosphere in an oven-dried apparatus. A heavy white precipitate formed immediately, and the resulting slurry was stirred for 15 min at 0° C. A solution of 3-butyn-1-ol (16.6 g, 0.236 mol) in anhydrous $CH_2Cl_2$ (80 mL) was added dropwise at 0° C. The slurry was warmed to room temperature and stirred for 2 h. Pentane (1000 mL) was added and the precipitated salts were filtered and washed with pentane. Fractional distillation of the combined filtrates gave 39.9 g (84% yield) of 3-butynyl triflate as a colorless liquid:

bp 25° C., 0.1 mm; lit bp 25° C., 0.1 mm; 300 mHz $^1$H NMR ($CDCl_3$) δ2.12 (t, J=2.6 Hz, 1H), 2.74 (dt, J=6.7, 2.6 Hz, 2H), 4.58 (t, J=6.7 Hz, 2H); 75 mHz $^{13}$C NMR ($CDCl_3$) δ118.67, 76.96, 73.66, 71.81, 19.95.

B. Synthesis of Ethyl α-(3-Butynyl)-3-pyridylacetate

To a stirred solution of anhydrous diisopropylamine (8.91 mL, 6.43 g, 63.5 mmol) in anhydrous THF (100 mL) was added 2.5M n-butyllithium in hexanes (25.4 mL, 63.5 mmol) at −20° C. under a dry argon atmosphere in an oven-dried apparatus. The resulting solution was stirred for 30 min at −20° C. A solution of ethyl 3-pyridylacetate (9.21 mL, 10.0 g, 60.5 mmol) in anhydrous THF (70 mL) was added to the LDA solution at −20° C. Hexamethylphosphoramide (20 mL) was added to dissolve the dark yellow precipitate The solution was stirred for 30 min at −20° C. and then 30 min at −78° C. A solution of the 3-butynyl triflate of Part A (12.9 g, 63.5 mmol) in anhydrous THF (30 mL) was added dropwise at −78° C. The resultant dark red solution was allowed to warm to room temperature and was stirred for 18 h. The reaction mixture was quenched by pouring it onto saturated $NH_4Cl$ (500 mL). The mixture was extracted with ether (3×500 mL). The combined extracts were washed with $H_2O$, saturated NaCl and dried ($MgSO_4$). The solvent was removed in vacuo to give a brown oil (24.8 g). Purification by silica gel (Aldrich catalog #22,719-6, 230–400 mesh) Chromatography using $CHCl_3/MeOH$ (99/1, v/v) afforded 10.6 g (81% yield) of product as a yellow oil ($R_f$=0.62, 95:5 (v/v) $CHCl_3/MeOH$, Bakerflex IBF-2 silica TLC plates):

300 mHz $^1H$ NMR ($CDCl_3$) δ1.22 (t, J=7.1 Hz, 3H), 2.15 (m, 4H), 3.82 (t, J=7.6 Hz, 1H), 4.15 (m, 2H), 7.27 (dd, J=8.2, 5.1 Hz, 1H), 7.67 (dt, J=8.0, 2.0 Hz, 1H), 8.54 (dd, J=4.8, 1.6 Hz, 1H), 8.57 (d, J=1.7 Hz, 1H); 75 mHz $^{13}C$ NMR ($CDCl_3$) δ173.13, 150.18, 149.34, 135.58, 134.40, 124.00, 82.92, 70.19, 61.60, 47.98, 32.09, 16.73, 14.47; chemical ionization mass spectrum ($CH_4$) m/z 218 (M+H)$^+$.

C. Synthesis of α-(3-Butynyl)-3-pyridylacetic Acid

1N NaOH (150 mL) was added dropwise to a stirred solution of ethyl α-(3-butynyl)-3-pyridylacetate of Part B (10.6 g, 48.8 mmol) in methanol (150 mL) at room temperature. The resulting yellow solution was stirred for 30 min. the methanol was removed in vacuo and the pH was adjusted to 5 with 1N HCl. The solution was concentrated in vacuo and then extracted with $CHCl_3$. The $CHCl_3$ extract was dried ($Na_2SO_4$) and the solvent was removed under reduced pressure to give 10.4 g of a yellow oil. Purification by recrystallization from $CH_2Cl_2$/hexane gave 7.93 g (86% yield) of the product as a white crystalline solid:

mp 109°–111° C.; 300 mHz $^1H$ NMR ($CDCl_3$) δ2.19 (m, 5H), 3.88 (t, J=7.5 Hz, 1H), 7.38 (dd, J=7.7, 5.1 Hz, 1H), 7.86 (dd, J=8.1, 1.8 Hz, 1H), 8.52 (dd, J=5.0, 1.4 Hz, 1H), 8.61 (s, 1H); 75 mHz $^{13}C$ NMR ($CDCl_3$) δ175.93, 148.03, 146.83, 138.24, 136.51, 124.83, 83.16, 70.36, 48.58, 32.13, 17.02; chemical ionization mass spectrum ($CH_4$) m/z 190 (M+H)$^+$.

D. Synthesis of (E)-6-(Bromomethylene)tetrahydro-3-(3-pyridyl)-2H-pyran-2-one Hydrochloride A mixture of N-bromosuccinimide (3.76 g, 21.1 mmol), potassium bicarbonate (2.12 g, 21.1 mmol) and α-(3-butynyl)-3-pyridylacetic acid of Part C (4.00 g, 21.1 mmol) in $CH_2Cl_2$(350 mL) was stirred for 4 h at room temperature in the dark. The mixture was added to 5% $Na_2S_2O_3$ (300 mL) to quench the reaction. The organic layer was washed with $H_2O$ and saturated NaCl and dried ($MgSO_4$). The solvent was removed in vacuo to give 5.2 g of a yellow oil. Purification by silica gel (Aldrich catalog #22,719-6, 230–400 mesh) chromatography using $CH_2Cl_2$/ethyl acetate (2:1, v/v) gave 0.60 g (11% yield) of the desired lactone as an oil ($R_f$=0.62, ethyl acetate, Bakerflex IBF-2 silica TLC plates). The lactone was characterized as the hydrochloride salt.

A solution of anhydrous HCl (0.75 mmol) in ethyl ether (50 mL) was added dropwise to a stirred solution of the lactone (200 mg, 0.746 mmol) in 1:1 anhydrous $CH_2Cl_2$/ether (200 mL) at room temperature. Removal of the solvent under reduced pressure gave a white solid. Recrystallization twice from methanol/ether gave 159 mg (70% yield) of the hydrochloride salt as colorless needles:

mp 170°–171° C., 300 mHz $^1H$ NMR ($CDCl_3$) δ2.22 (m, 1H), 2.34 (m, 1H), 2.76 (m, 1H), 2.97 (m, 1H), 4.43 (dd, J=12.8, 5.5 Hz, 1H), 5.24 (br s, 1H), 6.47 (t, J=2.0 Hz, 1H), 8.00 (dd, J=8.1, 5.5 Hz, 1H), 8.48 (dt, J=8.1, 1.7 Hz, 1H), 8.85 (dd, J=4.4, 1.1 Hz, 1H), 8.90 (d, J=1.8 Hz, 1H); 75 mHz $^{13}C$ NMR ($CDCl_3$) δ167.56, 151.82, 144.40, 143.06, 141.99, 137.12, 126.25, 91.49, 43.67, 24.06, 23.85; chemical ionization mass spectrum ($CH_4$) m/z (relative intensity) 268/270 (97/100, M+H), 240/242 (16/17), 188 (19). Anal. calcd. for $C_{11}H_{11}NO_2BrCl$: C, 43.28; H, 3.64; N, 4.60; Br, 26.24. Found: C, 43.01; H, 3.56; N, 4.52; Br, 26.38.

The chemical reactions described above are generally disclosed in terms of their broadest application to the preparation of the compounds utilized to practice the method of this invention. Occasionally, the reactions may not be applicable as described to each compound included within the disclosed scope. The compounds for which this occurs will be readily recognized by those skilled in the art. In all such cases, either the reactions can be successfully performed by conventional modifications known to those skilled in the art, e.g., by appropriate protection of interfering groups, by changing to alternative conventional reagents, by routine modification of reaction conditions, and the like, or other reactions disclosed herein or otherwise conventional, will be applicable to the preparation of the corresponding compounds of this invention. In all preparative methods, all starting materials are known or readily preparable from known starting materials.

The preceding examples can be repeated with similar success by substituting the generically or specifically described reactants and/or operating conditions of this invention for those used in the preceding examples.

EXAMPLE 11

The enol lactones of Examples 1-10 were utilized in the inhibition assays below.

The primary assay shows inhibition of purified calcium-independent canine myocardial $PLA_2$. This assay consists of determining the amount of radiolabeled fatty acid which is liberated from the radiolabeled phospholipid substrate by purified calcium-independent canine myocardial $PLA_2$ in the presence of varying concentrations of the inhibitor. The concentration of inhibitor which decreases the activity of the enzyme to 50% of the activity observed in the absence of that inhibitor is determined. This concentration is defined as the $IC_{50}$.

Several other $PLA_2$ assays were utilized in order to gain some measure of the selectivity of the inhibitors of calcium-independent myocardial $PLA_2$. Specifically, three other calcium-dependent mammalian $PLA_2$ assays are used: (1) sheep platelet $PLA_2$, (2) human synovial fluid PLA$_2$, and (3) porcine pancreatic PLA$_2$. The PLA$_2$ enzymes represent different groups of PLA$_2$ enzymes. Myocardial PLA$_2$, platelet PLA$_2$, and secreted PLA$_2$ enzymes (human synovial fluid PLA$_2$ and porcine pancreatic PLA$_2$) have very different calcium requirements, which may be typical of their respective classes.

An additional whole cell assay was also performed. In this assay, HL-60 cells are induced with the calcium ionophore A23187 in the presence of varying amounts of inhibitor, and the amounts of the prostaglandin E$_2$ (PGE$_2$) and leukotriene B$_4$(LTB$_4$) which form are measured. Calcium ionophore A23187 activates a calcium-dependent PLA$_2$ which leads to the enhanced production of the arachidonic acid metabolites PGE$_2$ and LTB$_4$. The concentrations of inhibitor which decrease the production of PGE$_2$ and LTB$_4$ by 50% relative to controls are expressed as IC$_{50}$ values. This assay, when inhibition is observed, suggests that the inhibitor enters the cell and inhibits a calcium-dependent PLA$_2$ or other enzyme in the arachidonate metabolic pathway which produces PGE$_2$ and LTB$_4$.

Calcium-Independent PLA$_2$ Assay

Purified canine myocardial cytosolic PLA$_2$ was isolated from an ATP-agarose eluate as described by Wolf, R. A., and Gross, R. W. J. Biol. Chem. 260, 7295–7303 (1985). The calcium-independent myocardial PLA$_2$ was incubated with selected concentrations ($10^{-10}$ to $10^{-4}$M) of test compound in 168 mM Tris-Cl, 6.4 mM EGTA (a calcium chelator) (pH 7.0) for 5 min at 25° C. Appropriate controls were performed in the absence of test compound. Catalysis was initiated by injection of 1 μM radiolabeled substrate (1-O-(Z)-(1′-hexadecenyl)-2-[9,10-$^3$H]-oleoyl-3-phosphorylcholine). After a 5 min incubation at 37° C., reaction products were extracted with n-butanol, separated by thin layer chromatography, and quantified by scintillation spectrometry. PLA$_2$ activity was compared in the presence and absence of test compound and the IC$_{50}$ was determined.

Calcium-Dependent PLA$_2$ Assays

Homogeneous sheep platelet cytosolic PLA$_2$ was prepared as described by Loeb, L. A., and Gross, R. W. J. Biol. Chem. 261, 10467–10470 (1986). The purified calcium-dependent platelet PLA$_2$ was preincubated in 70 mM Tris-Cl (pH 7.2) containing 1 μM CaCl$_2$ and test compound for 5 min at 25° C. Catalysis was initiated by injection 1 μM radiolabeled substrate (1-O-(Z)-(1′-hexadecenyl)-2-[9,10-$^3$H]-oleoyl-3-phosphorylcholine). After a 10 min incubation period at 37° C., reaction products were extracted with n-butanol, separated by thin layer chromatography, and quantified by scintillation spectrometry. PLA$_2$ activity was compared in the presence and absence of test compound and the IC$_{50}$ was determined.

Purified human synovial fluid PLA$_2$ (purified by the procedure of Fawzy, A. A. and Franson, R. C. Biophys. J. 49, 533a [1986]) was obtained from R. C. Franson (Medical College of Virginia, Richmond, Va.). PLA$_2$ activity was measured by using [$^{14}$C]-oleate labelled autoclaved E. coli as substrate as described by Franson, R. C., Patriarca, P., and Elsbach, P. J. Lipid Res. 15, 380–388 (1974). The assay was performed at 37° C. for 30 min in a final volume of 100 μL 50 mM Hepes buffer (pH 7.0) containing 150 mM NaCl, 5 mM CaCl$_2$, and E. coli cells (corresponding to 10 nmol phospholipid). The test compound or control vehicle was preincubated with PLA$_2$ for 5 min, followed by adding E. coli to initiate the reaction. The reaction was terminated by adding 2 mL tetrahydrofuran. The reaction product, [$^{14}$C]-oleic acid, was isolated using a 1 mL Bond Elute—NH$_2$ column and counted by liquid scintillation spectrometry.

Purified porcine pancreatic PLA$_2$ was obtained from Sigma (St. Louis, Miss.). PLA$_2$ activity was measured by using [$^{14}$C]-oleate labelled autoclaved E. coli as described by Franson, Patriarca and Elsbach (referenced above). The assay was performed at 37° C. for 5 min in a final volume of 100 μL Tris-HCl buffer (100 mM, pH 8.0) containing 1 mM EDTA, 10 mM CaCl$_2$, and E. coli (containing 10 nmol phospholipid). The test compound or control vehicle was preincubated with PLA$_2$ for 5 min, followed by adding E. coli to initiate the reaction. The reaction was terminated by adding 2 mL tetrahydrofuran. The reaction product, [$^{14}$C]-oleic acid, was isolated using a 1 mL Bond Elute—NH$_2$ column and counted by liquid scintillation spectrometry.

HL-60 Cell Assay for LTB$_4$ and PGE$_2$ Production

HL-60 cells grown exponentially in culture were induced to differentiate into granulocytes by a four day incubation with 0.8% (v/v) N,N-dimethylformamide. Prior to assay, differentiated HL-60 cells were washed once with Hanks' balanced salt solution containing 0.35 mg/mL sodium bicarbonate and 10 mM Hepes, pH 7.3 (HBSS) and resuspended in HBSS at a 3×10$^6$ cells/mL concentration. DMSO or test compounds solubilized in DMSO were added at 1:100 dilution to 1.0 mL HL-60 cell suspensions (3×10$^6$ cells) and preincubated at 37° C. for 10 min in a shaking water bath. After an additional 5 min incubation with 5×10$^{-6}$M calcium ionophore, A23187 (Calbiochem, La Jolla, Calif.), the cells were centrifuged at 12,800×g for 15 seconds and the supernatant (0.8 mL) removed and stored at −20° C. for LTB$_4$ and PGE$_2$ quantitation by radioimmunoassay (kits obtained from Amersham, United Kingdom and NEN Research Products, N. Billerica, Mass.).

Two conventions are used in the Table to indicate an approximate degree of inhibition when an IC$_{50}$ was not reached at the highest concentration of inhibitor: One greater than (>) symbol before the number indicates that inhibition was observed, but not quite enough for an IC$_{50}$. Two greater than symbols (>>) indicate little or no inhibition at the highest concentration used. Activation of an enzyme is indicated by a +X% which gave that activation of X%.

TABLE 1

| Example No. | Canine Heart PLA$_2$ IC$_{50}$(μM) | Sheep Platelet PLA$_2$ IC$_{50}$(μM) | HSF PLA$_2$ IC$_{50}$(μM) | Porcine Pancr. PLA$_2$ IC$_{50}$(μM) | HL-60 PGE$_2$ IC$_{50}$(μM) | HL-60 LTB$_4$ IC$_{50}$(μM) |
|---|---|---|---|---|---|---|
| 1 | 0.031 | 100 | >100 | >100 | >>100[1] | 11.7 |
| 2 | 0.095 | 38 | 53 | 17 | >10 | >10 |
| 3 | 0.14 | 72 | >>100 | >>100 | >>10[2] | >10 |
| 4 | 0.19 | — | — | — | — | — |
| 5 | 0.25 | >100 | >100 | 100 | >>100[3] | 1.1 |

TABLE 1-continued

| Example No. | Canine Heart PLA$_2$ IC$_{50}$(μM) | Sheep Platelet PLA$_2$ IC$_{50}$(μM) | HSF PLA$_2$ IC$_{50}$(μM) | Porcine Pancr. PLA$_2$ IC$_{50}$(μM) | HL-60 PGE$_2$ IC$_{50}$(μM) | HL-60 LTB$_4$ IC$_{50}$(μM) |
|---|---|---|---|---|---|---|
| 6 | 1.7 | — | — | — | — | — |
| 7 | 22.0 | — | — | — | — | — |
| 8 | 21.0 | — | — | — | — | — |
| 9 | (28%)[4] | — | — | — | — | — |
| 10 | 75 | — | — | — | — | — |

[1] +300%
[2] +91%
[3] +63%
[4] Inhibition at 100 μM

As shown in Example 11, enol lactones are capable of very potent and selective inhibition of calcium-independent canine myocardial PLA$_2$. Compound 1, an iodoenol lactone, is the most potent compound known against calcium-independent canine myocardial PLA$_2$, with an IC$_{50}$ of 0.031 μM. Compound 1 is highly selective as an inhibitor of calcium-independent canine myocardial PLA$_2$ and is over 3200-fold more selective for this enzyme over the calcium-dependent PLA$_2$ enzymes. The ynenol lactone 2 is over 170-fold more selective for inhibition of calcium-independent myocardial PLA$_2$ over the calcium-dependent PLA$_2$ enzymes; bromoenol lactone 3 is over 500-fold more selective and bromoenol lactone 5 is over 400-fold more selective. A series of structural variations allows some insight into the influence of various structural elements on enzyme inhibition of calcium-independent myocardial PLA$_2$. The trans-iodoenol lactone, 1, and the trans-bromoenol lactone, 3, are examples of extremely potent inhibitors of canine myocardial PLA$_2$. A need for the halogen is demonstrated by comparison with the compound of Example 7 which shows a loss of more than two orders of magnitude in potency when the halogen is not present. The potency drops off by almost an order of magnitude for the cis-iodoenol lactone 4 relative to the trans isomer, showing that the trans geometry at the exo iodomethylene group is also important. That the naphthyl group is important can be seen in comparisons with bromoenol lactones having other substituents, such as phenyl, phenoxy, hydrogen and pyridyl, 5, 8, 9 and 10. The IC$_{50}$ increases sharply across this series. Interactions of the enzyme with hydrophobic portions of the inhibitor may be considerable. The effect of lactone ring size can be seen in comparisons between 3 and 6: A six membered ring is much more potent than a five membered ring.

Furthermore, as shown by Example 11, the inhibitors utilized according to the present invention are selective inhibitors for calcium-independent PLA$_2$. It is contemplated that other enol lactones which fall under the formula set forth above will manifest activity similar to those exemplified herein.

As stated above, selective inhibition of calcium-independent PLA$_2$ is achieved utilizing the enol lactones of the formula set forth above. Thus, pharmaceutical compositions comprising one or more of the enol lactones can be administered for this purpose, utilizing an effective inhibitory amount of the compound(s) which amount can range from 1 nM to about 1 mM, such as from about 10 nM to about 100 μM, preferably from about 1 μM to about 50 μM. A most preferred effective amount is 10 μM. Such compositions, which may contain acceptable diluents and/or carriers, can be prepared by reference to general texts in the field such as, for example, Remington's Pharmaceutical Sciences, Ed Arthur Osol, 16th ed., 1980, Mack Publishing Co.

The foregoing is merely illustrative of the invention and is not intended to limit the invention to the disclosed compounds. Variations and changes which are obvious to one skilled in the art are intended to be within the scope and nature of the invention which are defined in the appended claims.

What is claimed is:

1. A method for treating a mammalian patient susceptible to cardiac injury, including ischemia and related infarction, from the activity of calcium-independent PLA$_2$ which comprises administering to said patient an effective inhibitory amount of a compound which selectively inhibits calcium-independent PLA$_2$ said compound represented by the formula

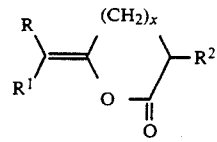

wherein R and R$^1$ independently represent hydrogen and radicals selected from the group consisting of halogen and alkyl, alkenyl, and alkynyl radicals; R$^2$ represents radicals selected from the group consisting of aryl, aryloxy, and heteroaryl radicals selected from aromatic monocyclic, bicyclic or tricyclic heterocycles containing one or more heteroatoms; and x represents 1 or 2.

2. Method of claim 1 wherein R and R$^1$ independently represent hydrogen, and halogen and alkynyl radicals.

3. Method of claim 1 wherein R and R$^1$ independently represent hydrogen and bromo, iodo and ethynyl radicals.

4. Method of claim 1 wherein R$^1$ represents hydrogen and R represents bromo, iodo and ethynyl radicals.

5. Method of claim 1 wherein R represents H and R$^1$ represents iodo.

6. Method of claim 1 wherein R$^2$ represents hydrogen and phenyl, phenoxy, naphthyl and pyridyl radicals.

7. Method of claim 2 wherein R$^2$ represents hydrogen and phenyl, phenoxy, naphthyl and pyridyl radicals.

8. Method of claim 3 wherein R$^2$ represents hydrogen, and phenyl, phenoxy, naphthyl and pyridyl radicals.

9. Method of claim 4 wherein R$^2$ represents hydrogen, and phenyl, phenoxy, naphthyl and pyridyl radicals.

10. Method of claim 5 wherein R$^2$ represents naphthyl.

11. Method of claim 1 wherein R represents bromo, iodo and alkynyl radicals; $R^1$ represents hydrogen; $R^2$ represents phenyl; and X is 2.

12. Method of claim 1 wherein R represents bromo, iodo and ethynyl radicals; $R^1$ represents hydrogen; $R^2$ represents phenoxy; and X is 2.

13. Method of claim 1 wherein R represents bromo, iodo and ethynyl radicals; $R^1$ represents hydrogen; $R^2$ represents naphthyl; and X is 2.

14. Method of claim 1 wherein R represents bromo, iodo and ethynyl radicals; $R^1$ represents hydrogen; $R^2$ represents pyridyl; and X is 2.

15. Method of claim 1 wherein R represents bromo, iodo and ethynyl radicals; $R^1$ represents hydrogen; $R^2$ represents phenyl, phenoxy, naphthyl and pyridyl radicals; and x is 1.

* * * * *